United States Patent
Binder et al.

(10) Patent No.: US 6,792,807 B2
(45) Date of Patent: Sep. 21, 2004

(54) METHOD AND APPARATUS FOR SENSING A SEAL ON A FILM

(75) Inventors: Francis J. Binder, Appleton, WI (US); Kenneth C. Radtke, Appleton, WI (US); Gaylord G. Guilette, Luxemburg, WI (US)

(73) Assignee: CMD Corporation, Appleton, MI (US)

( * ) Notice: Subject to any disclaimer, the term of this patent is extended or adjusted under 35 U.S.C. 154(b) by 0 days.

(21) Appl. No.: 09/840,369

(22) Filed: Apr. 23, 2001

(65) Prior Publication Data

US 2002/0152814 A1 Oct. 24, 2002

(51) Int. Cl.⁷ .................. G01N 29/04; B31B 49/04
(52) U.S. Cl. ................. 73/588; 73/584; 493/207
(58) Field of Search ............... 73/588, 587, 579, 73/643, 651, 661, 49.3, 159, 40, 52; 493/202, 207, 8, 11, 37

(56) References Cited

U.S. PATENT DOCUMENTS

| | | | |
|---|---|---|---|
| 3,825,750 A | * 7/1974 | Hayase et al. | 250/223 R |
| 4,580,438 A | * 4/1986 | Horand | 73/14 |
| 4,642,084 A | 2/1987 | Gietman, Jr. | 493/190 |
| 4,934,993 A | 6/1990 | Gietman, Jr. | 493/11 |
| 4,991,432 A | * 2/1991 | Houghton et al. | 73/159 |
| 5,226,316 A | * 7/1993 | Mally et al. | 73/49.3 |
| 5,285,678 A | * 2/1994 | McDaniel et al. | 73/49.3 |
| 5,292,299 A | 3/1994 | Anderson et al. | 493/11 |
| 5,447,486 A | 9/1995 | Anderson et al. | 493/11 |
| 5,488,480 A | 1/1996 | Saindon et al. | 356/429 |
| 5,518,559 A | 5/1996 | Saindon et al. | 156/64 |
| 5,587,032 A | 12/1996 | Saindon et al. | 156/64 |
| 5,649,569 A | * 7/1997 | De Jager et al. | 73/774 |
| 5,653,085 A | * 8/1997 | Suga | 53/75 |
| 5,660,674 A | 8/1997 | Saindon et al. | 156/353 |
| 5,808,199 A | * 9/1998 | Kazys et al. | 73/597 |
| 5,847,281 A | * 12/1998 | Kazys et al. | 73/597 |
| 5,861,078 A | 1/1999 | Huben et al. | |
| 6,028,318 A | * 2/2000 | Cornelius | 250/559.27 |
| 6,117,058 A | 9/2000 | Saunder et al. | 493/193 |
| 6,122,966 A | * 9/2000 | Goodman et al. | 73/593 |
| 6,131,452 A | * 10/2000 | Thalmann | 73/159 |
| 6,138,515 A | * 10/2000 | Moufle et al. | 73/639 |
| 6,339,961 B1 | * 1/2002 | Goodman et al. | 73/593 |
| 6,474,141 B1 | * 11/2002 | Takaoka et al. | 73/49.3 |
| 6,494,081 B1 | * 12/2002 | Moisio | 73/37.7 |

* cited by examiner

Primary Examiner—Hezron Williams
Assistant Examiner—Jacques M. Saint-Surin
(74) Attorney, Agent, or Firm—George R. Corrigan

(57) ABSTRACT

A method and apparatus for detecting seals on a film from which bags are formed includes a force transmitter and a force sensor. The force transmitter transmits a force from the film to the sensor. The force sensor receives the transmitted force and provides a force signal. A controller receives the force signal and provides a seal signal. The the force sensor may be an mechanical sensor, an acoustic sensor, a mechanical sensor, a vibration sensor or a piezoelectric sensor.

48 Claims, 2 Drawing Sheets

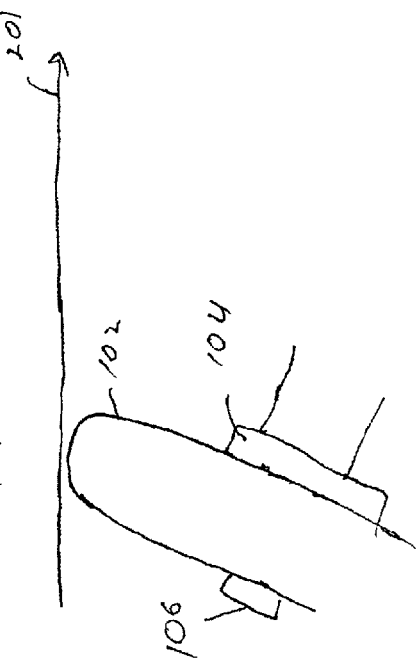
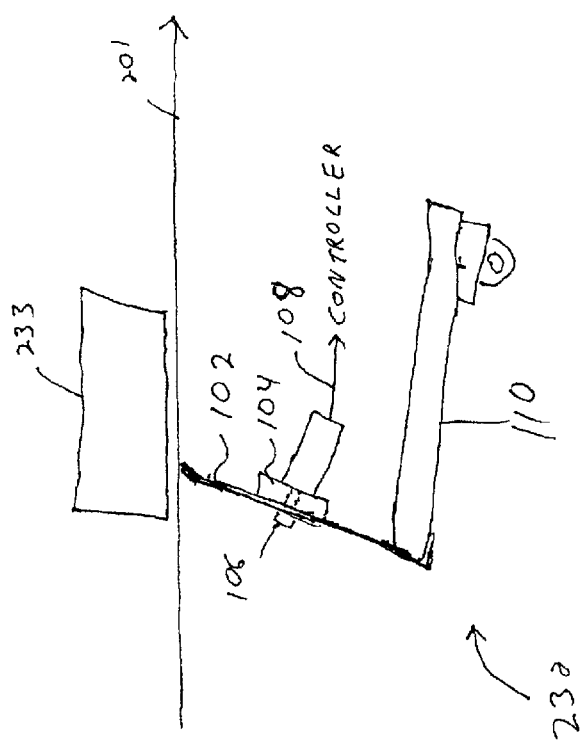

METHOD AND APPARATUS FOR SENSING A SEAL ON A FILM

FIELD OF THE INVENTION

The present invention relates generally to the art of bag making. More specifically, it relates to detecting a seal on a bag, and registration to that seal, such as for cutting, perforating etc.

BACKGROUND OF THE INVENTION

Many different types of plastic bag making machines are known in the art of producing plastic bags for industrial and individual consumers for many different applications (e.g. trash bags). While the present invention has a wide range of applications for the production of such products, the related art will be explained by reference to one particular class of bags i.e., polyethylene trash bags or, garbage bags and wastebasket liners of the type usually sold in boxes of folded bags or rolls of bags.

Examples of prior art machines can be found in U.S. Pat. No. 4,642,084 (the '084 patent) U.S. Pat. No. 4,934,993 (the '993 patent), which show generally a bag machine with a rotary sealing drum and U.S. Pat. No. 6,117,058, which shows a bag machine with a rotary sealing drum and servo-driven nips, devices, etc. U.S. Pat. Nos. 4,642,084, 4,934,993 and 6,117,058 are assigned to the owner of this invention and hereby incorporated by reference.

The control of the spacial relationship between a repetitive print pattern on the web and the repetitive seals, or the machine is placing across the web is referred to as the "registration" of the seal to the print on the web. This spacial relationship may also be referred to as the "phase" between the repetitive print and seal occurrences on the web.

Similarly, the control of the spatial relationship between the repetitive seals placed across the web and the repetitive perforations the machine is placing across the web is referred to as the "registration" of the perforation to the seal on the web. This spacial relationship may also be referred to as the "phase" between the repetitive perforations and the repetitive seals across the web. The distance between a seal and a perforation is commonly called the "skirt length" of the finished bag.

When a bag making machine such as that described in the '993 patent is used to adjust the drum diameter, any device (such as a perforator, knife, die cutter, punching station, or folding station) on the bag making machine that processes the plastic downstream of the drum may become out of proper synchronization with the sealing process occurring in the drum while the drum is changing diameter. A perforator, for example, slightly out of synchronization causes perforation to seal registration (skirt length) to vary. According to the '993 patent the skirt length may be adjusted manually. However, by the time the error is detected and the manual correction made, a considerable amount of film may be wasted.

U.S. Pat. No. 5,292,299 (the '299 patent), incorporated by reference, uses a proximity detector and an encoder to determine where each seal will be placed. However, the '299 patent does not actually sense and determine the location of a seal; the '299 patent "fixes" the distance between the point of application of the seal and the point of perforation at a constant minimum distance instead of detecting it.

One method of detecting a seal location includes burning a hole in the seal, or providing some other registration mark, and is described in U.S. Pat. No. 5,447,486, incorporated by reference. One significant drawback is that a notch or hole in the seal can be difficult to create, weaken the seal, of fail to be in a position to be detected.

Another prior art method located the seal with respect to a print mark, and then located the perforation to the print mark, thus indirectly locating the perforation with respect to the seal. However, the film path length between the location where the seal is created, and where the perforation is created can be relatively lengthy, thus this method is prone to error. Thus, it is desirable to directly place the perforation with respect to the seal.

U.S. Pat. Nos. 5,518,559, 5,488,480, 5,587,032, 5,660,674 and 5,861,078, hereby incorporated by reference, describe various attempts to register devices to a seal or print mark in bag making machines. Generally, they include optical detectors, that may be more effective than other prior art, but may be costly and/or complex, and still unable to detect all seals. U.S. Pat. No. 5,861,078 describes the use of a "window" to help reduce false positive detections. The general location of the seal is determined by the location of the seal bar (using encoders for example). Then, the seal sensor is activated for a short period of time (i.e, a window of time or film length) before and after the seal passes by the sensor. The exact location of the seal is then determined by the sensor. This improves the accuracy by eliminating false positives, but it does not decrease the likelihood of a seal being missed by the sensor.

Accordingly, a method and apparatus for detecting a seal is desirable. Preferably, it will not require marks, holes, notches, etc. to be made on the film. Further, it will be preferably be located near the a device which needs to be registered to the seal, and will include a window for greater accuracy.

SUMMARY OF THE PRESENT INVENTION

According to a first aspect of the invention an apparatus for detecting a seal on a film includes a force transmitter and a force sensor. The force transmitter transmits a force from the film to the sensor. The force sensor receives the transmitted force and provides a force signal. A controller receives the force signal and provide a seal signal.

According to a second aspect of the invention a bag machine includes a force transmitter, disposed to transmit a force responsive to a seal. A force sensor receives the transmitted force and provides a force signal. One or more processing devices are located upstream of the force transmitter and one or more processing devices are located downstream of the force transmitter. A controller receives the force signal and creates a seal signal.

According to various alternatives the force sensor is an mechanical sensor, an acoustic sensor, a mechanical sensor, a vibration sensor or a piezoelectric sensor.

An anvil is provided on a first side of a film path, and the force transmitter is on a second side of the film path in another embodiment.

The force transmitter is a quill, preferably rigid, disposed near a path of the film, and the quill may be angled downstream, and have a tip with a radius surface in other embodiments. The quill is held against the film path by a spring force in yet another embodiment.

The controller includes a window circuit in another alternative. The controller includes an amplitude comparator and/or a rise-time comparator in another alternative.

One of the downstream devices, such as a knife, is registered to the seal in another embodiment. The downstream devices and the force transmitter are in a common tension zone in yet another embodiment.

According to a third aspect of the invention a method for detecting a seal on a film includes providing a force signal responsive to the seal and detecting the force and providing a seal signal.

According to a fourth aspect of the invention a method of processing a bag includes transporting the film from a first processing device to a seal sensing location. Providing a force signal responsive to the seal at the seal sensing location. Then detecting the force and providing a seal signal, and transporting the film to a second processing device.

Various alternatives include transmitting a force from the film, preferably using a quill.

Other alternatives include detecting an acoustic, mechanical, or vibration signal.

The seal signal is provided in response to comparing an amplitude of the force with a threshold, and/or comparing a rise-time of the force with a threshold, and/or making such comparisons during a window in several embodiments.

Other principal features and advantages of the invention will become apparent to those skilled in the art upon review of the following drawings, the detailed description and the appended claims.

BRIEF DESCRIPTION OF THE DRAWINGS

FIG. 1 is a diagram of a seal sensor in accordance with the preferred embodiment;

FIG. 3 is a diagram of a quill used in the seal sensor of FIG. 1.

Figure 2:
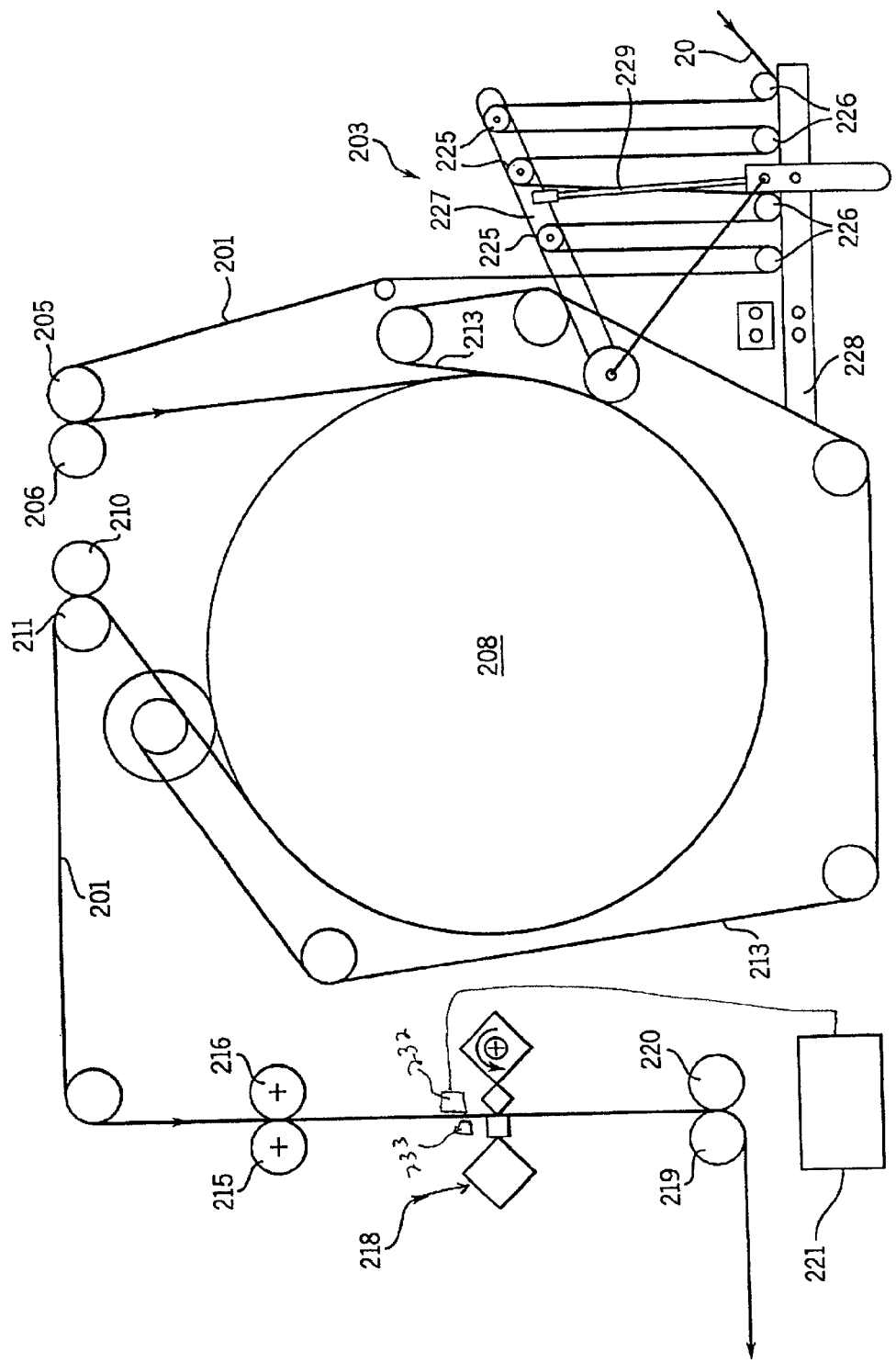
FIG. 2 is a diagram of a bag machine in accordance with the present invention.

Before explaining at least one embodiment of the invention in detail it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting. Like reference numerals are used to indicate like components.

DETAILED DESCRIPTION OF THE PREFERRED EMBODIMENTS

While the present invention will be illustrated with reference to a particular bag machine and sensor configuration, it should be understood at the outset that the invention may also be implemented with other bag machines, sensors, components, materials, etc.

Generally, the preferred embodiment includes sensing a seal on a moving plastic web or film using a vibrational pick up. A quill abutting the film vibrates and the mechanical vibration is converted into an electrical signal by means of a piezoelectric transducer (similar to the pick up on a phonograph). A controller (which includes software) analyzes the transducer output to determine when a seal is detected. The distance from the sensor quill to the knife is a known constant, and an encoder (such as a Rotopulser) gives linear film travel information to the controller. The controller controls the knife rotation to position the perforation in the desired location relevant to the seal (i.e. the correct registration). The location of the perforation to seal can be manually or automatically adjusted. The skirt lengths are stabilized and changes in seal to seal length are compensated for in the preferred embodiment. Further details will be provided below, after a description of the bag machine of the preferred embodiment.

The invention is implemented, in the preferred embodiment, with a rotary drum bag machine such as one described in the prior art referenced above, and shown in FIG. 2. However, the invention may be implemented with other types of bag machines may be used as well. Bag machine, as used herein, includes a machine that forms a bag, such as by placing seals on a tubular film, or processes already made bags.

The bag machine of FIG. 2 process a film 201, and includes a dancer assembly 203, a pair of drum-in rolls 205 and 206, a sealing drum 208, a pair of drum-out rolls 210 and 211, a sealing blanket 213, a pair of knife-in rolls 215 and 216, a knife 218 (which could be any other film processing device such as a perforator, die cutter, punching station, folding station, etc), a pair of knife-out rolls 219 and 220, and a controller 221.

Dancer assembly or processing device 203 includes a plurality of upper rolls 225 and lower rolls 226. Processing device, as used herein, includes a device used in bag machines, including dancer assemblies, sealers, drive rolls, knives, perforators, folders, stackers, etc. Rolls 225 and 226 are mounted on arms 227 and 228, which are pivotally inter-connected. The vertical distance between rolls 225 and 226 is controlled to control the tension on the web.

After leaving dancer assembly 203 film 201 is directed or transported to drum-in rolls 205 and 206. (Transporting the film, as used herein, includes moving a film or bags from a first location in a machine to a second.) Roll 205 is a servo-driven roll in the preferred embodiment, and roll 206 is an idler roll in the preferred embodiment. Of course, other roll arrangements may be used as well. The film is then directed to sealing drum 208.

Sealing drum 208 may be a typical sealing drum although the particular type of drum, nor even the use of a drum to seal, is important for the present invention.

Drum-out rolls 210 and 211 are used to slow down film 201, and reintroduce tension. Roll 211 is preferably a servo driven roll, and rolls 210 and 211 are both rubber wrapped rolls. Of course, other roll arrangements may be used as well.

After film 201 leaves drum 208 and drum-out rolls 210 and 211, it is transported past a seal sensor, including an anvil 233 and sensor 232 Sensor 232 preferably senses changes in amplitude of the films surface—such as those formed by seals. Sensor 232 will be described in detail below. Thereafter, film 201 is transported to knife or processing device 218. Processing device 218 is upstream of sensor 232 in an alternative embodiment. Processing device 218 is registered to the seal. Registered to the seal, as used herein, includes a device or processing station that performs an operation on the film, wherein the operation is registered to a seal.

The distance between the sensor quill and knife is preferably less than the shortest bag length (although it could be more than one bag length from the sensor with appropriate software/control). Also, seal sensor 232 is in a common tension zone with processing device 218. Common tension zone, as used herein, includes a length of the film path where the tension is substantially constant, such as between two nips.

Controller 221 has control outputs (not shown) connected to the various servo and other driven rolls, the air regulator that controls air cylinder 229, dancer assembly 203, drum 208 (which includes outputs to the seal bars and/or the blanket drives), knife 218 and seal sensor 232 to control these elements. Controller 221 includes a touch pad, in the preferred embodiment, that allows the user to input various control parameters and a PLC. Other microprocessor or analog based controllers could be used, and controller 221 may control fewer or more components. Also, controller 221 may be a single controller in a single location, or distributed in various locations, or multiple controllers. Controller, as used herein, includes digital and/or analog circuitry and hardware and/or software used to control a machine or process.

Additional details of the bag machine of FIG. 2 may be found in U.S. Pat. No. 6,117,058.

Referring now to FIG. 1, a diagram of sensor 232 and anvil 233 is shown. Sensor 232 includes a quill 102 and a piezoelectric sensor 104 mounted thereon.

Quill, as used herein, includes a device used to detect changes in amplitude on the surface of the film. Piezoelectric sensor, as used herein, includes a sensor that provides an electric signal in response to an applied or sensed force.

Piezoelectric sensor 104 is mounted on quill 102 using a bolt 106. The output of piezoelectric sensor 104 is provided to controller 221 (FIG. 2) on a wire 108. Part of controller 221 may be located with piezoelectric sensor 104, such as comparators, discrimination circuits etc. Quill 102 is mounted on a bracket 110. Bracket 100 exerts a spring force on quill 102, so that it abuts the path of film 201, and is held against film 201. Alternatively, quill 102 may be gravity balanced.

Abutting the film path, as used herein, includes placement in or near the film path, such that the film (when present) is touched, grazed, or almost touched. Held against the film, as used herein, includes a force holding a structure such that it abuts the film path. Spring force, as used herein, includes a force exerted in a desired direction.

Bracket 100 is preferably made of aluminum, and mounted on one end on a rod so that it slides in a cross-machine direction. Quill 102 is preferably made of stainless steel, or other rigid material, and piezoelectric sensor 104 is a PCB Piezotronics U353B33 or 209M67 sensor in the preferred embodiment. The structure and location of the components of sensor 232 are, shown (and described) for the preferred embodiment, but they could be implemented with arrangements as well.

Anvil 233 is placed on the side of the film opposite quill 102 in the preferred embodiment, and it increases the ability of the quill to detect surface irregularities in the film. (Anvil, as used herein, includes a structure which provides support opposite the sensor.) Anvil 233 may be omitted or in any number of configurations and comprised of various materials, such as rubber. The surface of anvil 233 that contacts the film can be covered with Teflon®, and anvil 233 may be about 4–5 inches by 11 inches, and about ¾ inches thick.

Anvil 233 and pivot arm mechanism or bracket 110 may be mounted to a common mass plate, which provides vibration isolation from the mount. The mount preferably slides in the cross machine direction allow the anvil/quill to be aligned with the edge of the film. The vibration isolation decouples the mass plate from machine vibration and prevents unwanted mechanical noise from influencing the sensor. This provide a high signal to machine noise ratio.

A plough guard upstream from the quill may be sued to prevent film knots from causing damage to the sensor unit, and/or a pneumatic cylinder could also move the quill off the film in various alternatives.

Referring now to FIG. 3, a diagram showing quill 102 being held against film 102 is shown. Pivot arm or bracket 110 is preferably angled to the film surface such that the quill is angled downstream, about 20 degrees relative to normal. (Angled downstream relative to normal, as used herein, includes the downstream end being closer to the film path than the upstream end.) The tip of quill 102 has a radius surface of about 0.25" with a width of 0.14" in the machine direction. (Radius surface, as used herein, includes a curved surface). This helps prevent damage to the quill. Also, the angular alignment, quill contact tip radius and width influence the signal to film noise ratio. They are preferably chosen to provide a desirable signal to noise ratio.

When a seal passes quill 232, the uneven surfaces of the seal (i.e., changes in amplitude of the surface) vibrate or mechanically move quill 102. Alternatively, an acoustic vibration could be sensed. The seal surface irregularities can be caused by differences in film thickness and coefficient of friction. Quill 232 is a force transmitter and transmits the changing force from the surface irregularities to sensor 104. Force transmitter, as used herein, includes a structure or device that receives a force in one location and provides a force indicative of that force to another location.

The mechanical vibration is converted into an electrical signal by piezoelectric transducer or force sensor 104. The electric signal is referred to as force signal. Force signal, as used herein, includes a signal indicative of a force applied, and the signal may be a force or it may be of some other nature, such as electrical. Force sensor, as used herein, includes a sensor that detects a force or a change in force and/or provides a signal in response thereto. In response thereto, as used herein, includes providing a signal that is indicative of a signal received or detected.

The electric signal (a voltage) is provide to controller 221 which amplifies it and provides the amplified signal to a rise-time comparator (such as an RC circuit on the input of an op amp, or an active filter, or a digital filter). The rise-time comparator filters out slow changes in amplitude (or slow vibrations), such as those cause by something other than the seal.

Then, if the rise-time comparator determines the signal has a rise time consistent with a seal, the signal is rectified and provided to an amplitude comparator, along with a threshold signal. The amplitude comparator filters signals having an amplitude smaller than a seal. These filters help prevent false positive detections. Thus, sensor 232 senses the seal on a moving web via vibrational or mechanical pick up, and is a mechanical, vibration or acoustic sensor.

Mechanical sensor, as used herein, includes a sensor that detects and/or provides a signal in response to, a mechanical force, wave, vibration etc. Acoustic sensor, as used herein, includes a sensor that detects sound or acoustic ways or forces. Vibration sensor, as used herein, includes a sensor work that detects and/or provides a signal in response to a vibration.

Amplitude comparator, as used herein, includes analog and/or digital circuitry, and hardware and/or software that compares the signal representative of amplitude with another signal. Rise-time comparator backspace, as used herein, includes digital and/or analog circuitry, and hardware and/or software that compares a signal indicative of rise-time with another signal.

If the signal meets the rise-time and amplitude thresholds, a 20 msec pulse or seal signal is provided that indicates a seal is detected. Seal signal, as used herein, include a signal that indicates the presence and/or location of the seal. The leading edge of the pulse corresponds to the seal location, and the remainder is used to prevent second and third seal detections of the same seal, or detections between seals. The portion of controller 102 that filters the signal may be implemented using hardware or software, and may be located remotely from, or adjacent sensor 232.

The preferred embodiment includes a window circuit that provides a window in which the sensor is active, to decrease false positive detections. Window circuit, as used herein, includes a circuit, analog or digital, hardware or software, that creates a window, in time or in location on a film, in which to detect a seal. The general location of the seal is determined by the location of the seal bar (using encoders for example). Then, the seal sensor is activated for a short period of time before and after the seal passes by the sensor. Thus, the exact location of the seal is determined and changes in the film path length from the drum to the knife can be compensated for, and the skirt length minimized. Increased sensitivity may be provided with a window, because the window reduces false positives.

The window may be determined by many methods in other embodiments, including using a proximity switch on the sealing drum and encoder pulses, a registration mark, manually adjusting the skirt length and creating a window surrounding the desired length. The window may alternatively be created using a pulse having a duration slightly less than the time it takes for one bag to pass the detector. For example, a web or film traveling 600 fpm travels 1.5 feet in 150 msec. Thus, if the pulse duration is set at 150 msec (rather than 20 msec), the seal sensor does not become active 18 inches have passed. A 24 inch bag would then have a window of six inches for detection.

Other alternatives include using a capacitance sensor rather than the mechanical sensor.

Numerous modifications may be made to the present invention which still fall within the intended scope hereof. Thus, it should be apparent that there has been provided in accordance with the present invention a method and apparatus for a bag machine with a seal sensor that fully satisfies the objectives and advantages set forth above. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The embodiments of the invention in which an exclusive property or privilege is claimed are defined as follows:

1. An apparatus for detecting a seals formed between successive bags on a film moving in a machine direction, comprising;
    a force transmitter, disposed to transmit a force from the film, wherein the force is created when the film moves in the machine direction with respect to the force transmitter;
    a force sensor disposed to receive the transmitted force and provide a force signal in response thereto; and
    a controller, disposed to receive the force signal and provide a seal signal indicative of the presence and location of the seal in response thereto.

2. The apparatus of claim 1, wherein the force sensor is an acoustic sensor.

3. The apparatus of claim 1, wherein the force sensor is a mechanical sensor.

4. The apparatus of claim 1, wherein the force sensor is a vibration sensor.

5. The apparatus of claim 1, further comprising an anvil disposed on a first side of a film path, wherein the force transmitter is disposed on a second side of the film path.

6. The apparatus of claim 1, wherein the force sensor is a piezoelectric sensor.

7. The apparatus of claim 5, wherein the force transmitter is a quill disposed near a path of the film.

8. The apparatus of claim 6, wherein the quill is rigid.

9. The apparatus of claim 7, wherein the quill is comprised of stainless steel.

10. The apparatus of claim 6, wherein the quill is angled in a downstream film path direction, relative to normal to the film path.

11. The apparatus of claim 10, wherein the quill includes a radius surface abutting the film path, and the quill is held against the film path by a spring force.

12. The apparatus of claim 5, wherein the controller includes an amplitude comparator that receives the force signal and an amplitude threshold.

13. The apparatus of claim 5, wherein the controller includes a rise-time comparator that receives the force signal and a rise-time threshold.

14. The apparatus of claim 1, wherein the controller includes a window circuit.

15. A method for detecting a seal formed between successive bags on a film moving in a machine direction, comprising;
    creating a force when the film moves in the machine direction relative to a sensor;
    providing a force signal responsive to the seal; and
    detecting the force and providing a seal signal indicative of the presence and location of the seal in response thereto.

16. The method of claim 15, further comprising transmitting a force from the film.

17. The method of claim 15, wherein providing the force signal includes detecting an acoustic signal.

18. The method of claim 16, wherein providing the force signal includes detecting a mechanical signal.

19. The method of claim 16, wherein providing a force signal includes sensing a vibration.

20. The method of claim 15, further comprising transmitting the force with a quill disposed near a path of the film.

21. The method of claim 15, wherein providing a seal signal includes comparing an amplitude of the force with a threshold.

22. The method of claim 21, wherein providing a seal signal includes making the comparison during a window.

23. The method of claim 22, wherein providing a seal signal includes comparing a rise-time of the force with a threshold.

24. An apparatus for detecting a seal formed between successive bags on a film moving in a machine direction, comprising;
    means for providing a force signal in response to the seal and a force, wherein the force is created when the film moves in the machine direction;
    means for detecting the force signal, coupled to the means for providing a force signal; and
    means for providing a seal signal indicative of the presence and location of the seal in response to the force signal, coupled to the means for detecting.

25. The apparatus of claim 24, further comprising means for transmitting a force from the film to the means for detecting, coupled to the means for detecting.

26. The apparatus of claim 25, wherein the means for detecting includes means for detecting an acoustic signal.

27. The apparatus of claim 25, wherein the means for detecting includes means for detecting a mechanical signal.

28. The apparatus of claim 25, wherein the means for detecting includes means for detecting a vibration signal.

29. The apparatus of claim 25, wherein the means for providing a seal signal includes means for comparing an amplitude of the force with a threshold.

30. The apparatus of claim 29, wherein the means for providing a seal signal includes means for making the comparison during a window.

31. The apparatus of claim 30, wherein the means for providing a seal signal includes means for comparing a rise-time of the force with a threshold.

32. A machine, comprising;
   a force transmitter, disposed to transmit a force responsive to a seal formed between successive bags on a continuous film moving in a machine direction, wherein the force is created as the bag moves in the machine direction relative to the transmitter;
   a force sensor disposed to receive the transmitted force and provide a force signal in response thereto;
   at least one upstream processing device, located upstream of the force transmitter;
   at least one downstream processing device, located downstream of the force transmitter; and
   a controller, disposed to receive the force signal and provide a seal signal indicative of the presence and location of the seal in response thereto.

33. The apparatus of claim 32, wherein the force sensor is a mechanical sensor.

34. The apparatus of claim 32, further comprising an anvil disposed on a first side of a film path, wherein the force transmitter is disposed on a second side of the film path.

35. The apparatus of claim 34, wherein the force sensor is a piezoelectric sensor.

36. The apparatus of claim 35, wherein the force transmitter is a quill disposed near a path of the film.

37. The apparatus of claim 36, wherein the quill is angled downstream.

38. The apparatus of claim 37, wherein the quill includes a radius surface abutting the film path, and the quill is held against the film path by a spring force.

39. The apparatus of claim 38, wherein the controller includes a window circuit.

40. The apparatus of claim 32, wherein one of the at least one downstream devices is registered to the seal.

41. The apparatus of claim 40, wherein one of the at least one downstream devices includes a knife.

42. The apparatus of claim 40, wherein one of the at least one downstream devices and the force transmitter are in a common tension zone.

43. A method for processing a plurality of bags formed from successive seals on a continuous film, comprising;
   transporting the film from a first processing device to a seal sensing location, and past the seal sensing location in a machine direction;
   providing a force signal responsive to the seal and a force at the seal sensing location, wherein the force is created by the seal moving in the machine direction;
   detecting the force and providing a seal signal indicative of the presence and location of the film in response thereto;
   transporting the film to a second processing device.

44. The method of claim 43, further comprising transmitting a force from the film.

45. The method of claim 44, wherein providing the force signal includes detecting a mechanical signal.

46. The method of claim 43, wherein providing a seal signal includes comparing an amplitude of the force with a threshold.

47. The method of claim 46, wherein providing a seal signal includes making the comparison during a window.

48. The method of claim 43, wherein providing a seal signal includes comparing a rise-time of the force with a threshold.

* * * * *